(12) United States Patent
Yamano et al.

(10) Patent No.: US 9,402,683 B2
(45) Date of Patent: Aug. 2, 2016

(54) SUBMUCOSAL LAYER DISSECTION INSTRUMENT, SUBMUCOSAL LAYER DISSECTION SYSTEM, AND SUBMUCOSAL LAYER DISSECTION METHOD

(75) Inventors: Hiro-o Yamano, Akita (JP); Akihito Sadamasa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1013 days.

(21) Appl. No.: 11/014,538

(22) Filed: Dec. 16, 2004

(65) Prior Publication Data

US 2005/0149099 A1 Jul. 7, 2005

(30) Foreign Application Priority Data

Dec. 19, 2003 (JP) ................. P 2003-422693

(51) Int. Cl.
*A61M 29/00* (2006.01)
*A61B 18/14* (2006.01)
*A61B 1/018* (2006.01)
*A61B 17/29* (2006.01)
*A61B 17/34* (2006.01)
*A61B 17/00* (2006.01)
*A61B 18/00* (2006.01)

(52) U.S. Cl.
CPC ............ *A61B 18/1492* (2013.01); *A61B 1/018* (2013.01); *A61B 17/29* (2013.01); *A61B 17/3478* (2013.01); *A61B 18/1402* (2013.01); *A61B 2017/00269* (2013.01); *A61B 2018/0022* (2013.01); *A61B 2018/00214* (2013.01); *A61B 2218/002* (2013.01)

(58) Field of Classification Search
CPC ............ A61B 1/018; A61B 17/3478; A61B 2218/002; A61B 2017/00269; A61B 19/24; A61B 1/00082; A61B 5/6853; A61B 2018/0022; A61B 2017/320048
USPC .......... 606/198, 159, 190–192; 600/207, 115, 600/116
See application file for complete search history.

(56) References Cited

U.S. PATENT DOCUMENTS

| 4,517,976 | A | * | 5/1985 | Murakoshi et al. ............. 606/46 |
| 5,301,682 | A | * | 4/1994 | Debbas ........................ 600/550 |
| 5,324,269 | A | * | 6/1994 | Miraki ......................... 604/160 |
| 5,766,151 | A | * | 6/1998 | Valley et al. .............. 604/103.07 |

(Continued)

FOREIGN PATENT DOCUMENTS

| JP | 11-146881 | 6/1999 |
| JP | 2003-153911 | 5/2003 |
| WO | WO 93/04727 | 3/1993 |

OTHER PUBLICATIONS

Ono, H. et al., "Important Techniques for EMR Using an IT Knife for Early Cancer", Journal of the Japan Gastroenterological Endoscopy Society (2002), vol. 14, No. 11, pp. 1737-1740, together with English-language translation.

*Primary Examiner* — Katherine Rodjom
(74) *Attorney, Agent, or Firm* — Scully, Scott, Murphy & Presser, PC

(57) ABSTRACT

A submucosal layer dissection instrument of the present invention includes an instrument body that is inserted into a submucosal layer, a line formed between the proximal end side and the distal end side of the instrument body; and an expanding section provided on the distal end side of the instrument body that expands in the case of having received a supply of fluid through the line.

13 Claims, 14 Drawing Sheets

(56) References Cited

U.S. PATENT DOCUMENTS

| | | | |
|---|---|---|---|
| 5,795,325 A | 8/1998 | Valley et al. | |
| 5,851,210 A * | 12/1998 | Torossian | 606/108 |
| 6,007,483 A * | 12/1999 | Kieturakis | 600/115 |
| 6,146,401 A * | 11/2000 | Yoon et al. | 606/192 |
| 6,193,692 B1 * | 2/2001 | Harris et al. | 604/164.02 |
| 6,338,345 B1 * | 1/2002 | Johnson et al. | 128/897 |
| 6,860,892 B1 * | 3/2005 | Tanaka et al. | 606/190 |
| 7,047,981 B2 * | 5/2006 | Durgin | 128/898 |
| 7,185,657 B1 * | 3/2007 | Johnson et al. | 128/898 |
| 7,300,448 B2 * | 11/2007 | Criscuolo et al. | 606/190 |
| 7,481,800 B2 * | 1/2009 | Jacques | 604/264 |
| 2001/0012934 A1 * | 8/2001 | Chandrasekaran et al. | 606/41 |
| 2001/0049497 A1 | 12/2001 | Kalloo et al. | |
| 2001/0049509 A1 * | 12/2001 | Sekine et al. | 604/264 |
| 2003/0225460 A1 * | 12/2003 | Gostout et al. | 623/23.72 |
| 2004/0138682 A1 * | 7/2004 | Onuki et al. | 606/144 |
| 2005/0004592 A1 * | 1/2005 | Criscuolo | 606/190 |
| 2006/0173483 A1 * | 8/2006 | Kieturakis et al. | 606/192 |

* cited by examiner

SUBMUCOSAL LAYER DISSECTION INSTRUMENT, SUBMUCOSAL LAYER DISSECTION SYSTEM, AND SUBMUCOSAL LAYER DISSECTION METHOD

Priority is claimed on Japanese Patent Application No. 2003-422693, filed Dec. 19, 2003, the contents of which are incorporated herein by reference.

BACKGROUND OF THE INVENTION

1. Field of the Invention

The present invention relates to a submucosal layer dissection instrument, a submucosal layer dissection system, and a submucosal layer dissection method for resecting an affected area of the digestive tract using an endoscope.

2. Description of the Related Art

Endoscopic mucosal resection (EMR), in which a lesion is resected using an endoscope, is typically employed for treatment of lesions of the digestive tract.

A method in which normal mucosa around an affected area is completely incised using a high-frequency knife such as a high-frequency scalpel followed by dissection and resection of the submucosal layer is introduced as an endoscopic submucosal dissection method of this type of endoscopic mucosal resection (see, for example, Reference 1 below).

[Reference 1] Ono, H. et al., "Important Techniques for EMR Using an IT Knife for Early Cancer", Journal of the Japan Gastroenterological Endoscopy Society, Japan Gastroentero-logical Endoscopy Society Editorial Committee, Tokyo Igakusha Publishing, November 2002, Vol. 14, No. 11, pp. 1737-1740.

Furthermore, other high-frequency scalpels used in other treatment differing from that described above are proposed in Reference 2 below.

[Reference 2] U.S. Patent Application, Publication No. US2001/0049497A1

When performing incision and dissection using a conventional instrument described above, since there are numerous blood vessels running through the submucosal layer, special considerations are required such as constantly having to change the output setting of the high-frequency cauterization power supply that supplies high-frequency current to the high-frequency scalpel whenever the scalpel is near any of these blood vessels.

In addition, in order to realize a suitable incision while preventing heat damage to the area being incised due to the high-frequency energy during incision and dissection using a high-frequency scalpel, it is necessary to suitably control the force and angle by which the knife is pressed against the tissue, the speed at which the knife is moved and so forth.

SUMMARY OF THE INVENTION

A submucosal layer dissection instrument of the present invention includes an instrument body that is inserted into a submucosal layer, a line formed between the proximal end side and the distal end side of the instrument body, and an expanding section provided on the distal end side of the instrument body that expands in the case of having received a supply of a fluid through the line.

An insertion path into which a high-frequency scalpel is inserted may be provided along the line.

The instrument body may include a supply flow path for liquid to be injected into the submucosal layer.

The insertion path may also serves as a supply flow path for liquid injected into the submucosal layer.

The distal end of the instrument body may have a shape such that it tapers towards the distal end, and the location of the distal end of the expanding section during expansion may be made to coincide with the location of the distal end of the instrument body.

An indicator that indicates the amount of insertion of the distal end of the insertion body may be provided on the instrument body on the proximal end side than the expanding section.

A submucosal layer dissection system of the present invention includes an endoscope in which a first channel and a second channel are provided, the abovementioned submucosal layer dissection instrument that is inserted into the first channel, and a submucosal injection needle inserted into the second channel, which injects a liquid into the submucosal layer.

Another submucosal layer dissection system of the present invention includes an endoscope in which a first channel and a second channel are provided, the abovementioned submucosal layer dissection instrument that is inserted into the first channel, and a grasping forceps inserted into the second channel, which supports the submucosal layer.

A first submucosal layer dissection method of the present invention includes an insertion step in which the abovementioned submucosal layer dissection instrument is inserted into elevated submucosal layer, and a dissection step in which the expanding section of the submucosal layer dissection instrument is expanded by supplying a fluid thereto followed by dissection of the submucosal layer.

The first submucosal layer dissection method may further include a hemostasis step in which an area of bleeding of the submucosal layer is stopped from bleeding by applying pressure with the expanding section.

A second submucosal layer dissection method of the present invention includes a hole opening step in which a hole is opened in mucosa that covers a submucosal layer with a high-frequency incision instrument, an insertion step in which the distal end of the instrument body of the abovementioned submucosal layer dissection instrument is inserted into the hole, a dissection step in which the submucosal layer is dissected by supplying a fluid into the expanding section to expand it, and an incision step in which at least one of the mucosa around the hole and the submucosal layer is incised using the high-frequency incision instrument.

A third submucosal layer dissection method of the present invention includes a hole opening step in which a hole is opened in mucosa that covers a submucosal layer with a high-frequency incision instrument, an insertion step in which the distal end of the instrument body of the abovementioned submucosal layer dissection instrument which includes the supply flow path for liquid to be injected into the submucosal layer, is inserted into the hole, a dissection step in which the submucosal layer is dissected by supplying a fluid into the expanding section to expand it, an incision step in which at least one of the mucosa around the hole and the submucosal layer is incised using the high-frequency incision instrument, and a liquid injection step in which the liquid is injected into the supply flow path to elevate the submucosal layer.

The third submucosal layer dissection method may further include an irrigation step in which bleeding within the submucosal layer is irrigated by injecting the liquid into the supply flow path.

A fourth submucosal layer dissection method of the present invention includes: a hole opening step in which a hole is opened in mucosa that covers a submucosal layer with a high-frequency incision instrument; an insertion step in which the distal end of the instrument body of the abovementioned submucosal layer dissection instrument which has a shape such that it tapers towards the distal end, and in which the location of the distal end of the expanding section during expansion be made to coincide with the location of the distal end of the instrument body, is inserted into the hole; a positioning step in which the location of the distal end of the instrument body is aligned with the dissected location of the submucosal layer; a dissection step in which the submucosal layer is dissected by supplying a fluid into the expanding section to expand it; and an incision step in which at least one of the mucosa around the hole and the submucosal layer is incised using the high-frequency incision instrument.

A fifth submucosal layer dissection method of the present invention includes: a hole opening step in which a hole is opened in mucosa that covers a submucosal layer with a high-frequency incision instrument; an insertion step in which the distal end of the instrument body of the abovementioned submucosal layer dissection instrument in which the indicator that indicates the amount of insertion of the distal end of the insertion body be provided on the instrument body on the proximal end side than the expanding section, is inserted into the hole; a positioning step in which the location of the distal end of the instrument body is aligned with the dissected location of the submucosal layer based on the indicator; a dissection step in which the submucosal layer is dissected by supplying a fluid into the expanding section to expand it; and an incision step in which at least one of the mucosa around the hole and the submucosal layer is incised using the high-frequency incision instrument.

A sixth submucosal layer dissection method of the present invention includes an elevation step in which the submucosal layer is elevated by injecting a liquid into the submucosal layer using the submucosal injection needle of the abovementioned submucosal layer dissection system, an insertion step in which the submucosal layer dissection instrument is inserted into the elevated submucosal layer, and a dissection step in which the submucosal layer is dissected by supplying a fluid into the expanding section of the submucosal layer dissection instrument to expand it.

A seventh submucosal layer dissection method of the present invention includes a support step in which the submucosal layer is supported using the grasping forceps of the abovementioned another submucosal layer dissection system, an insertion step in which the submucosal layer dissection instrument is inserted into the elevated submucosal layer, and a dissection step in which the submucosal layer is dissected by supplying a fluid into the expanding section of the submucosal layer dissection instrument to expand it.

DETAILED DESCRIPTION OF THE INVENTION

Figure 1:
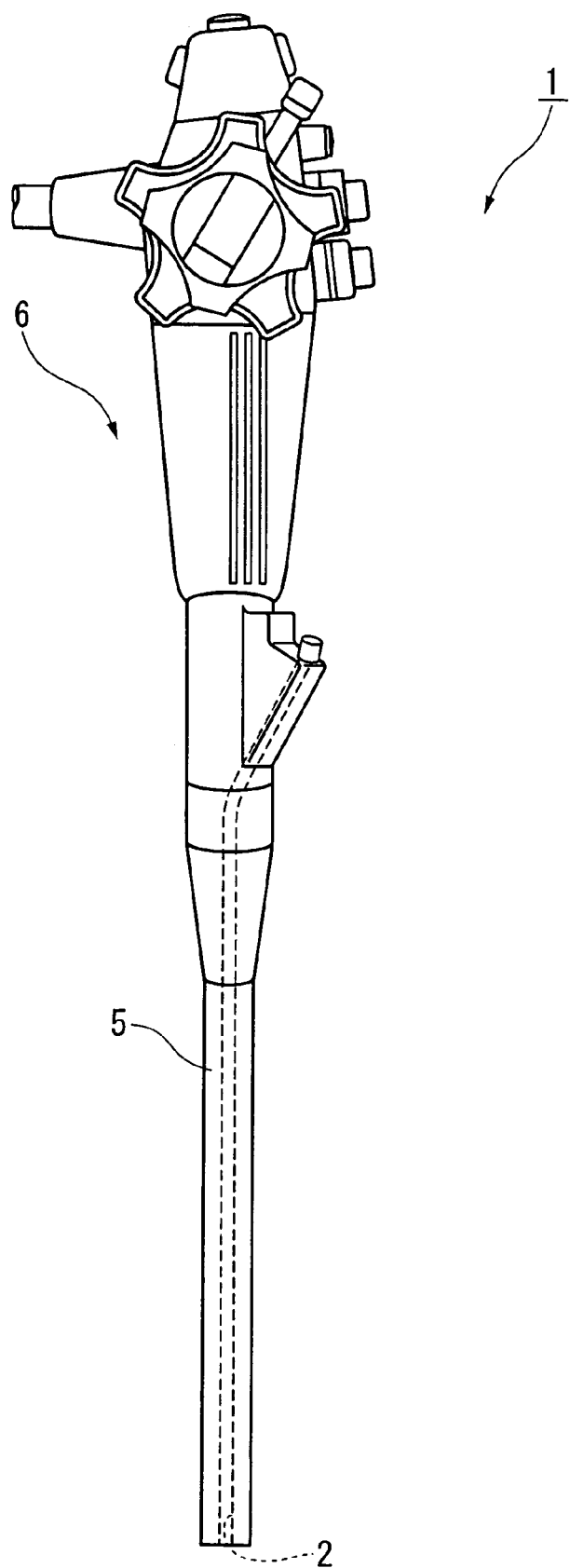
FIG. 1 is a side view of an endoscope of a submucosal layer dissection system according to a first embodiment of the present invention.

The following provides an explanation of a first embodiment of the present invention with reference to FIGS. 1 through 14.

A submucosal layer dissection system 1 of the present embodiment is provided with an endoscope 6 (see FIG. 1) in which a channel 2 is arranged within an insertion section 5, a dissection balloon (submucosal layer dissection instrument) 7 (see FIG. 2) that can be inserted into channel 2, and a submucosal injection needle 8 (see FIG. 7) that can be inserted into channel 2 and is able to inject a liquid into a submucosal layer.

Figure 2:
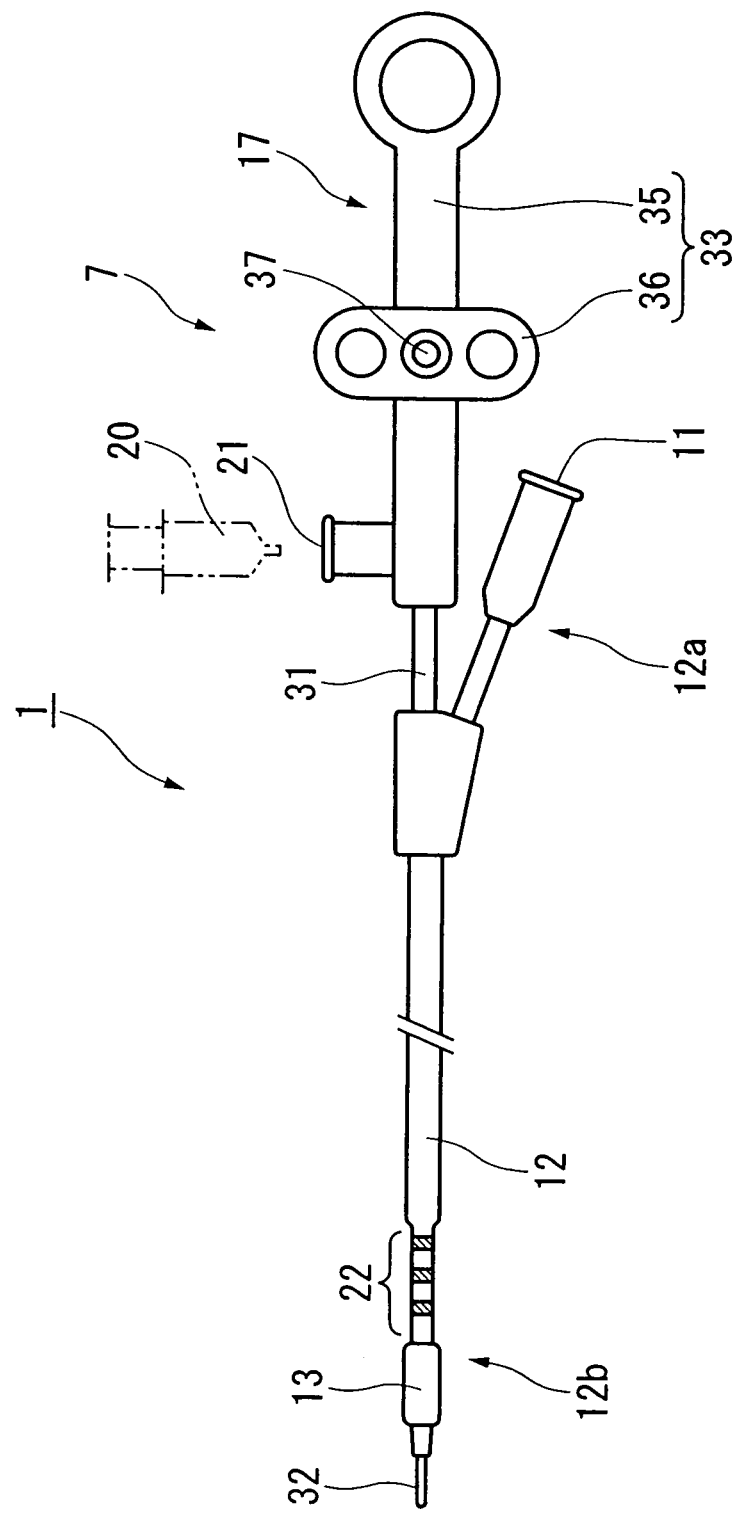
FIG. 2 is a side view of a dissection balloon of the same submucosal layer dissection system.
Figure 3:
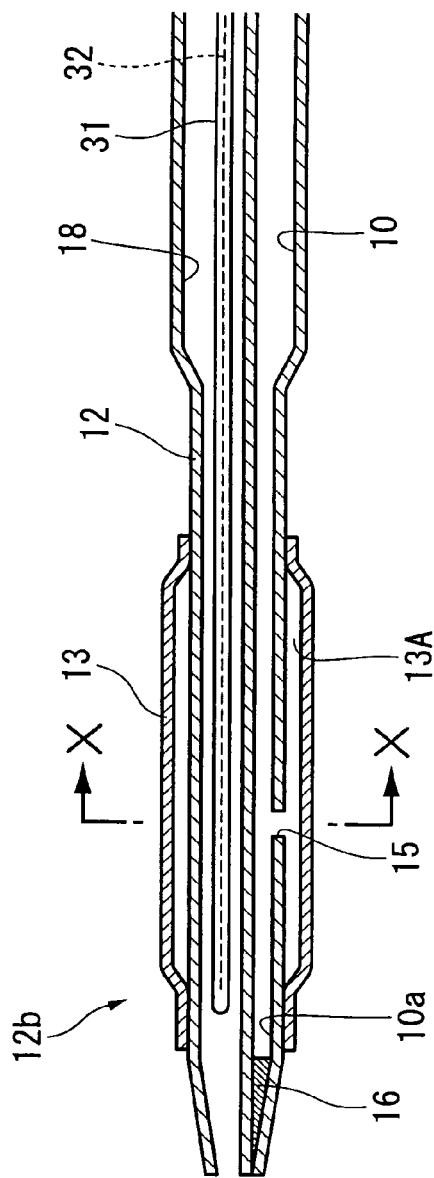
FIG. 3 is a partial cross-sectional view of a dissection balloon of the same submucosal layer dissection system.
Figure 4:
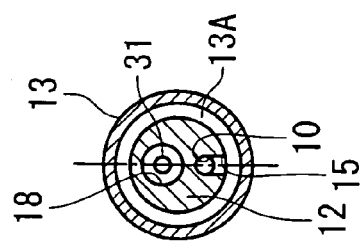
FIG. 4 is a cross-sectional view taken along X-X of FIG. 3.

Dissection balloon 7 ablates a submucosal layer by inserting the distal end into the submucosal layer in order to resect an affected area of the digestive tract using an endoscope. As shown in FIGS. 2 through 4, dissection balloon 7 is provided with an instrument body 12 in which a line 10 is provided so as to extend in the axial direction and in which an injection port 11 that is continuous with line 10 is provided on the side of proximal end 12a, and a balloon (expanding section) 13 provided around the distal end 10a of line 10 that can be expanded by a gas or liquid supplied into gap 13A from injection port 11.

A communicating hole 15 that connects line 10 and gap 13A inside balloon 13 is provided in the section on the side of instrument body 12 covered with balloon 13. Distal end 10a of line 10 is sealed by a sealing member 16. Due to this sealing member 16, gas or liquid supplied to line 10 flows into balloon 13 through communicating hole 15 without leaking from distal end 10a of line 10.

In addition, an insertion path 18 that allows the passage of a high-frequency scalpel (high-frequency incision instrument) 17 is provided along line 10 inside instrument body 12. This insertion path 18 allows a liquid injected into the submucosal layer to pass through. In addition, a liquid injection port 21 that can be connected to a syringe (liquid supply source) 20 that supplies a liquid is provided on the proximal end side of insertion path 18, and this can also be used as a flow path for the supplied liquid.

Figure 5:
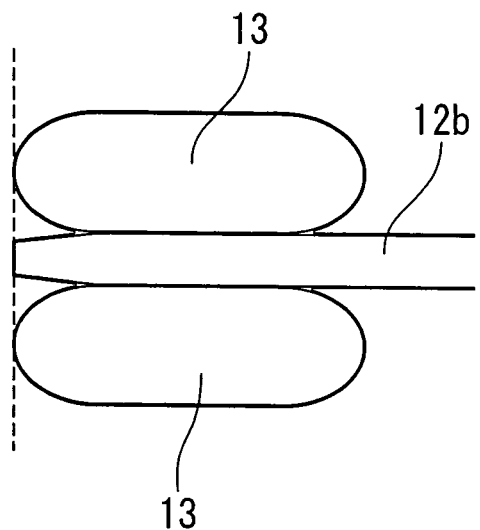
FIG. 5 is a side view showing the state in which the dissection balloon of the same submucosal layer dissection system has been expanded.

Distal end 12b of instrument body 12 is formed to a shape such that the outer diameter gradually decreases towards distal end 12b. As shown in FIG. 5, the location of the distal end of instrument body 12 coincides with the location of the distal end of balloon 13 when expanded.

Figure 6:
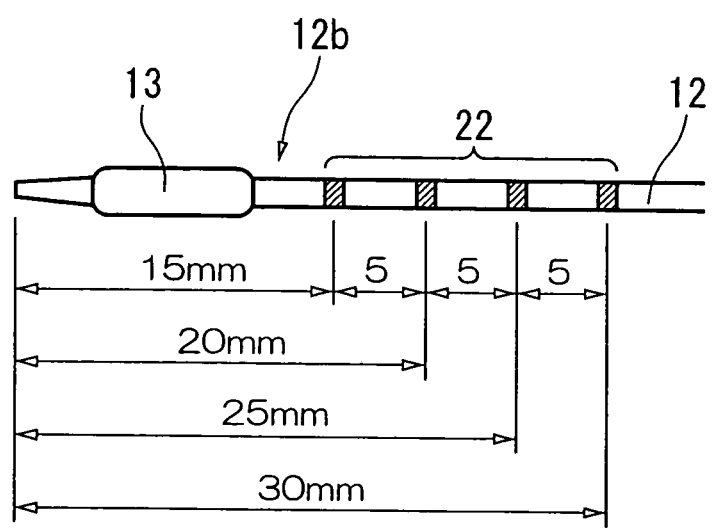
FIG. 6 is a side view of the distal end of the dissection balloon of the same submucosal layer dissection system.

As shown in FIG. 6, an indicator 22 that indicates the amount of insertion of distal end 12 at 5 mm intervals along the range of 30 mm from the location of the distal end is provided on the outer periphery of instrument body 12 on the side more proximal than balloon 13.

Figure 7A:
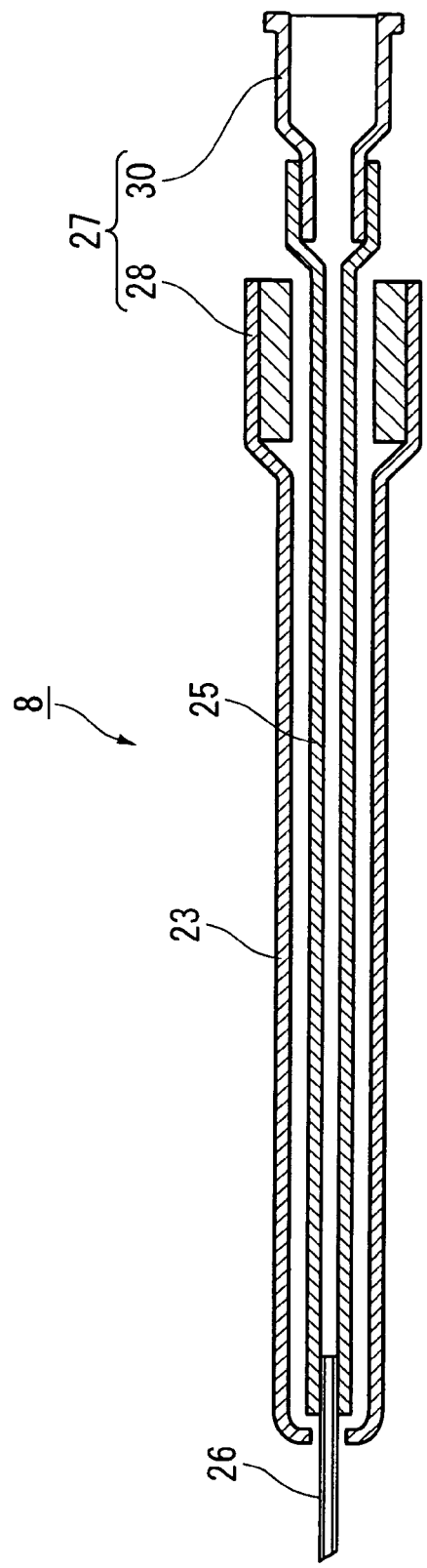
FIGS. 7A and 7B are cross-sectional views of a submucosal injection needle of the same submucosal layer dissection system.
Figure 7B:
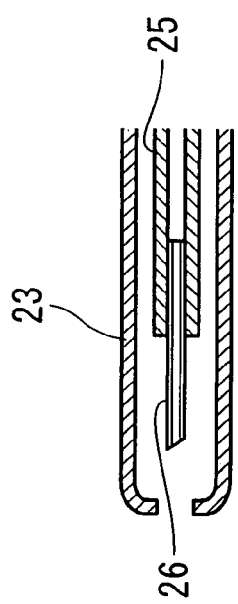
Figure 8:
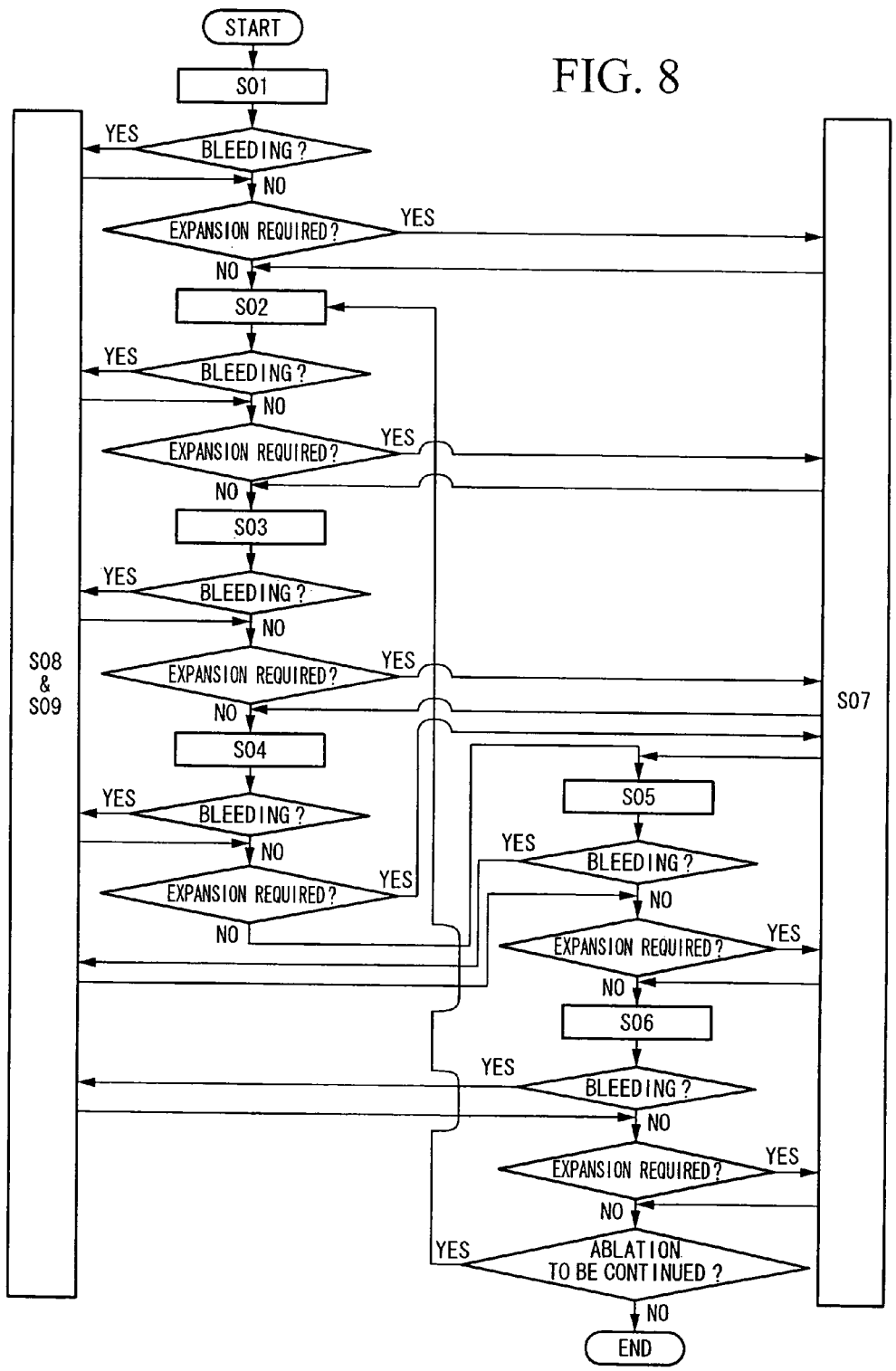
FIG. 8 is a flowchart showing a method for dissecting a submucosal layer using the same submucosal layer dissection system.

As shown in FIGS. 7A and 7B, submucosal injection needle 8 is provided with an outer tube 23, an inner tube 25 that advances and retracts within this outer tube 23, a needle body 26 attached to the distal end of inner tube 25 and which is formed to be hollow, and a needle operating section 27 attached to the proximal end of outer tube 23.

The distal end of outer tube 23 is formed into substantially a hemispherical shape, and a through hole is formed that only allows needle body 26 to pass through inner tube 25.

Needle operating section 27 is provided with a needle operating section body 28 attached to the proximal end of outer tube 23, and a cap 30 attached to the proximal end of inner tube 25 for injecting a liquid for local injection (local injection liquid). Needle body 26 can be protruded from the distal end of outer tube 23 by moving cap 30 relative to needle operating section body 28.

As shown in FIG. 2, high-frequency scalpel 17 is provided with an operating tube 31 formed into the shape of a tube, a high-frequency knife 32 retractably provided in operating tube 31 and formed into the shape of a needle, and a knife operating section 33 connected to the proximal end of operating tube 31.

Knife operating section 33 is provided with a knife operating section body 35, and a sliding section 36 connected to the proximal end of high-frequency knife 32 and able to be moved forward and backward with respect to knife operating section body 35. A connector 37 which is connectable to a high-frequency power supply (not shown in the figures) is provided in sliding section 36.

Next, a procedure using submucosal layer dissection system 1 according to the present embodiment along with its operation and effect will be explained.

In a method for dissecting a submucosal layer using this submucosal layer dissection system 1, a submucosal layer 40 is dissected by inserting the distal end of dissection balloon 7 into submucosal layer 40 in order to resect an affected area 38 of the digestive tract using an endoscope. Namely, as shown in FIGS. 8 through 13, a dissection method of a submucosal layer has an elevation step (S01) in which an affected area 38 of the digestive tract is elevated by injecting a liquid into submucosal layer 40 using a submucosal injection needle 8, a hole opening step (S02) in which a hole 41 is opened in mucosa 42 using a high-frequency scalpel 17 in the elevated submucosal layer 40, an insertion step (S03) in which the distal end 12b of instrument body 12 is inserted into hole 41, a positioning step (S04) in which the location of the distal end of instrument body 12 is aligned with the dissected location of submucosal layer 40 while visually confirming an indicator 22, a dissection step (S05) in which submucosal layer 40 is dissected by expanding balloon 13 of dissection balloon 7 by supplying a gas or liquid thereto, an incision step (S06) in which at least one of mucosa 42 around hole 41 and submucosal layer 40 is incised using high-frequency scalpel 17, a liquid injection step (S07) in which a liquid is injected from an injection port into an insertion path 18 to elevate affected area 38, a hemostasis step (S08) in which bleeding from the affected area that has occurred in any of the previous steps is stopped by applying pressure as a result of expanding balloon 13, and an irrigation step (S09) in which the area of bleeding is irrigated.

Figure 9A:
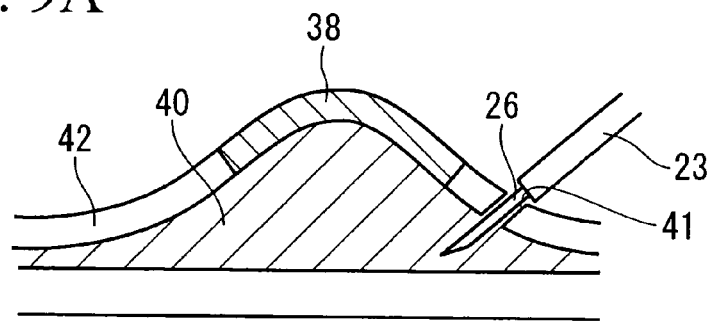
FIGS. 9A through 9C are cross-sectional views showing a method for dissecting a submucosal layer using the same submucosal layer dissection system.

In the aforementioned elevation step (S01), the distal end of endoscope 6, in which submucosal injection needle 8 is inserted into channel 2, is first brought close to affected area 38. Subsequently, the distal end of outer tube 23 of submucosal injection needle 8 is made to protrude from the distal end of channel 2. Moreover, by moving cap 30 towards the distal end relative to needle operating section body 28, needle body 26 is made to protrude from the distal end of outer tube 23 as shown in FIG. 9A, and puncture submucosal layer 40 from mucosa 42. A local injection liquid such as physiological saline is then injected into inner tube 25. An artificial protuberance is then formed at affected area 38 by injecting the local injection liquid into submucosal layer 40.

Following elevation, needle body 26 is returned to the inside of inner tube 25 by moving cap 30 towards the proximal end. Then, submucosal injection needle 8 is then withdrawn from channel 2.

Next, the procedure proceeds to the hole opening step (S02).

Figure 9B:
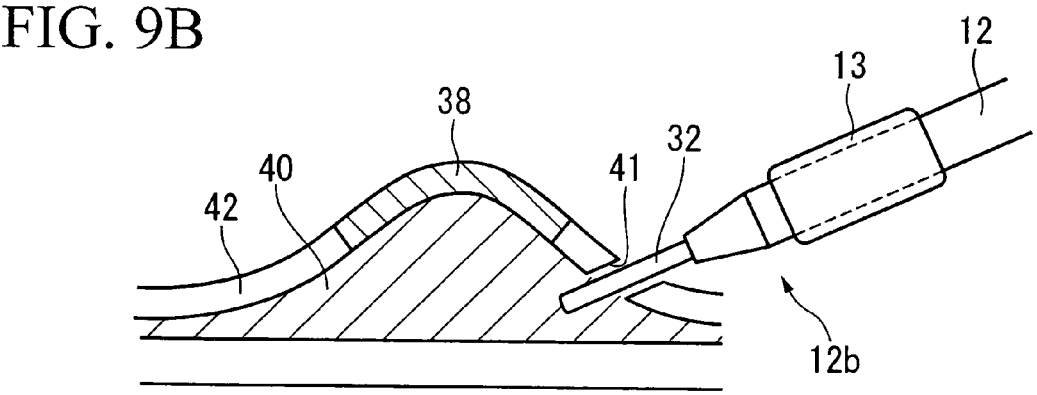

First, dissection balloon 7 is inserted into channel 2 and the distal end of dissection balloon 7 is made to protrude from the distal end of channel 2. High-frequency knife 32 is made to protrude by moving sliding section 36 towards the distal end relative to knife operating section body 35. While in this state, hole 41 is opened in mucosa 42 by advancing high-frequency knife 32 as shown in FIG. 9B while supplying a high-frequency current from the aforementioned high-frequency power supply connected to connector 37.

After hole 41 has been opened, the supply of high-frequency current is terminated and high-frequency knife 32 is housed in operating tube 31 by moving sliding section 36 towards the proximal end. Moreover, high-frequency scalpel 17 is housed in insertion path 18.

Once hole 41 has reached a certain depth, the procedure proceeds to the insertion step (S03) in which distal end 12b of instrument body 12 is inserted into hole 41.

Figure 9C:
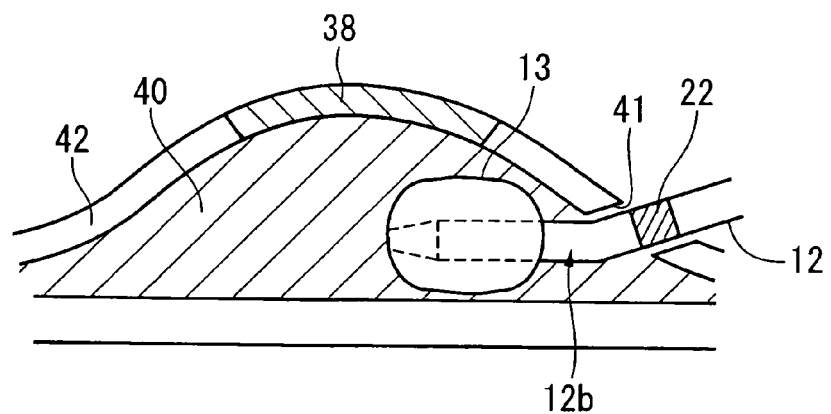

The procedure then proceeds to the positioning step (S04) in which the location of the distal end of instrument body 12 is aligned with the location where submucosal layer 40 is desired to be dissected while observing indicator 22 with endoscope 6. In the present embodiment, for example, the distal end of instrument body 12 is inserted to the location just before the first graduation from the distal end is hidden within hole 41 as shown in FIG. 9C.

While in this state, the procedure proceeds to the dissection step (S05).

First, the pressure inside line 10 is increased since the distal end 10a of line 10 is sealed with sealing member 16 when a gas or liquid is introduced into line 10 from injection port 11. Next, balloon 13 is expanded by introducing a gas or liquid into balloon 13 through communicating hole 15. As a result, submucosal layer 40 is dissected as a result of pressure being applied to its periphery as shown in FIG. 9C.

Figure 10A:
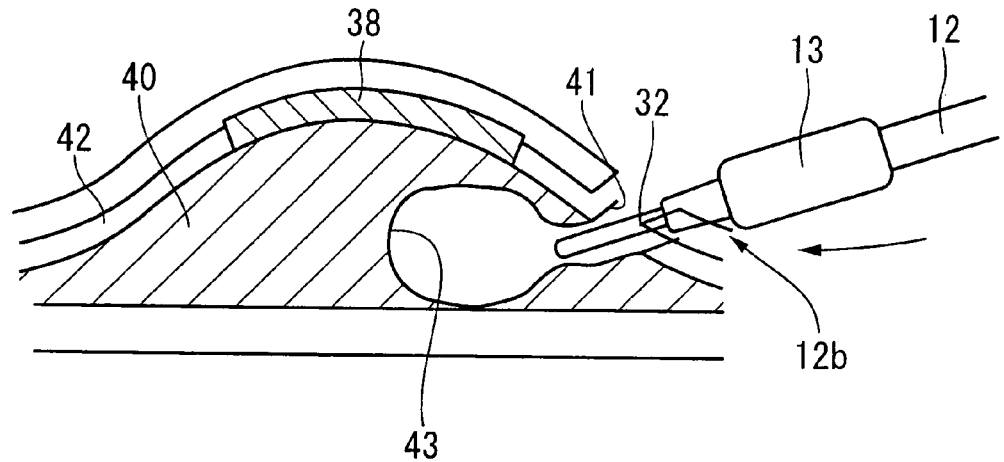
FIGS. 10A through 10C are cross-sectional views showing a method for dissecting a submucosal layer using the same submucosal layer dissection system.

At this time, since the distal end of balloon 13 and the distal end 12b of instrument body 12 are at nearly the same location, when balloon 13 is contracted by discontinuing the inflow of gas or liquid and releasing the gas or liquid from injection port 11, submucosal layer 40 is dissected to a location at which the distal end is a desired depth from the surface of mucosa 42 as shown in FIG. 10A, resulting in the formation of a first cavity 43.

Continuing, the procedure, proceeds to the incision step (S06).

Figure 10B:
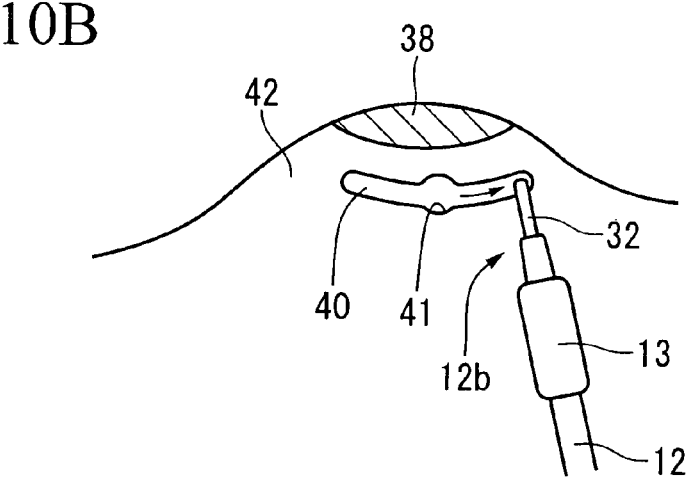

Instrument body 12 is retracted outside hole 41. High-frequency knife 32 is then inserted into first cavity 43 by causing high-frequency scalpel 17 to protrude from the distal end of insertion path 18. At least one of mucosal 42 around hole 41 and submucosal layer 40 is incised by moving high-frequency knife 32 from hole 41 along the periphery of affected area 38 as shown in FIG. 10B while supplying a high-frequency current from a high-frequency power supply while in this state.

After an incision had made of a certain width, the supply of high-frequency current is terminated. After housing high-frequency knife 32 in operating tube 31, high-frequency scalpel 17 is housed in insertion path 18.

Next, the procedure returns to the hole opening step (S02). The distal end of dissection balloon 7 is inserted into hole 41, and high-frequency scalpel 17 is made to protrude from inside insertion path 18 towards the back of first cavity 43. High-frequency knife 32 is then made to protrude and hole 41 is opened to a predetermined depth in mucosa 42 and submucosal layer 40 while advancing high-frequency scalpel 17.

The procedure then proceeds to the insertion step (S03) in which the distal end 12a of instrument body 12 is inserted into newly opened hole 41.

Figure 10C:
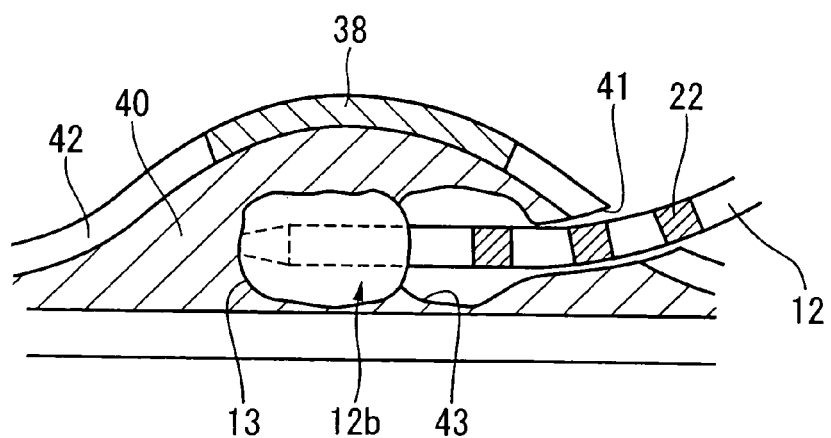

Next, in the positioning step (S04), distal end 12b of instrument body 12 is aligned at the location desired to be dissected while visually confirming indicator 22. In the present embodiment, for example, distal end 12b of instrument body 12 is inserted to the location where the second graduation from the distal end is hidden within hole 41 as shown in FIG. 10C.

Figure 11A:
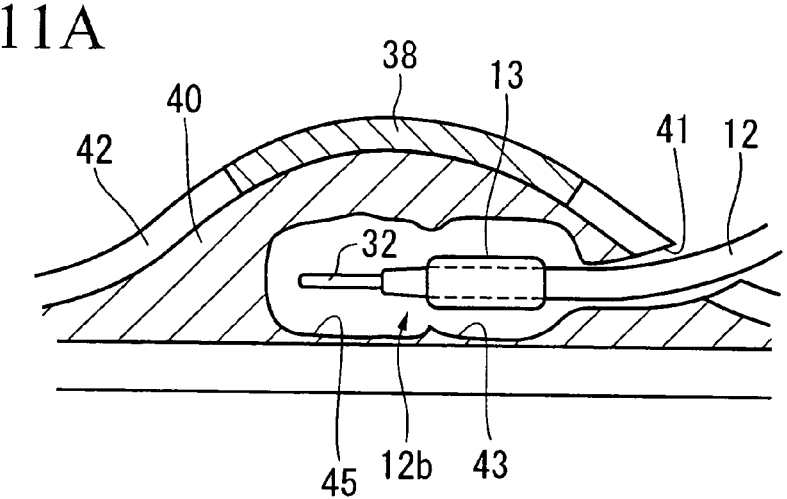
FIGS. 11A through 11C are cross-sectional views showing a method for dissecting a submucosal layer using the same submucosal layer dissection system.

Next, the procedure proceeds to the dissection step (S05) in which balloon 13 is expanded by introducing a gas or liquid from injection port 11 into line 10. As a result, submucosal layer 40 is dissected while pressure is applied towards its periphery. As a result, as shown in FIG. 11A, a second cavity 45 is formed behind first cavity 43.

Next, the procedure proceeds to the incision step (S06). After high-frequency scalpel 17 has protruded from the distal end of insertion path 18, high-frequency knife 32 is inserted into second cavity 45. While in this state, high-frequency knife 32 is moved along the periphery of affected area 38 from hole 41 while supplying a high-frequency current from the high-frequency power supply to make an incision in at least one of mucosa 42 around hole 41 and submucosal layer 40.

After having been incised to a certain width, the supply of high-frequency current is terminated. After high-frequency knife 32 is housed in operating tube 31, high-frequency scalpel 17 is housed in insertion path 18.

Figure 11B:
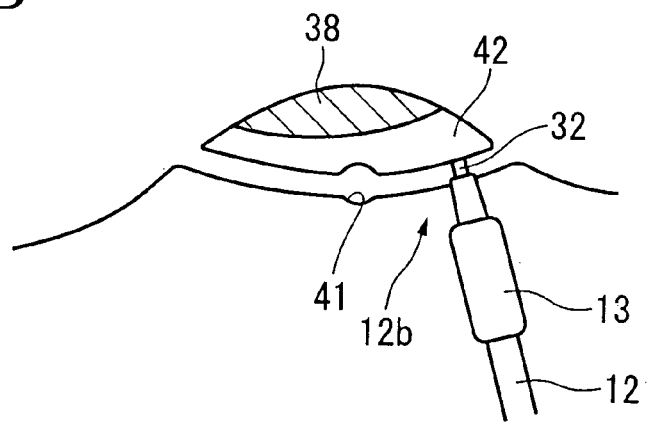
Figure 11C:
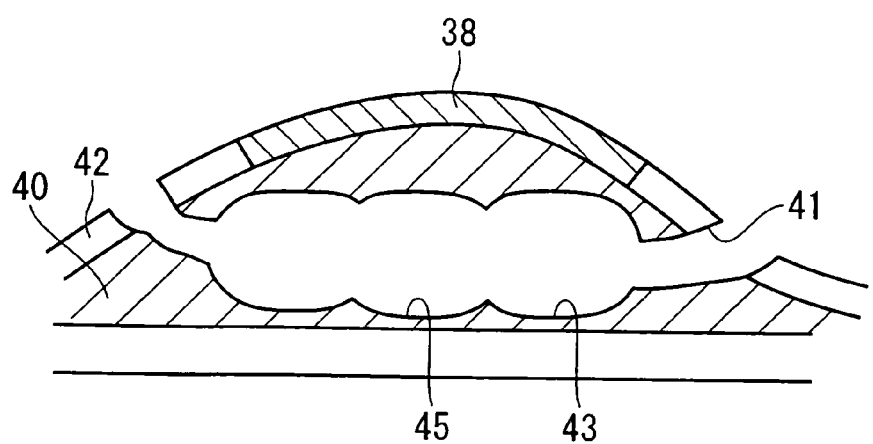
Figure 12:
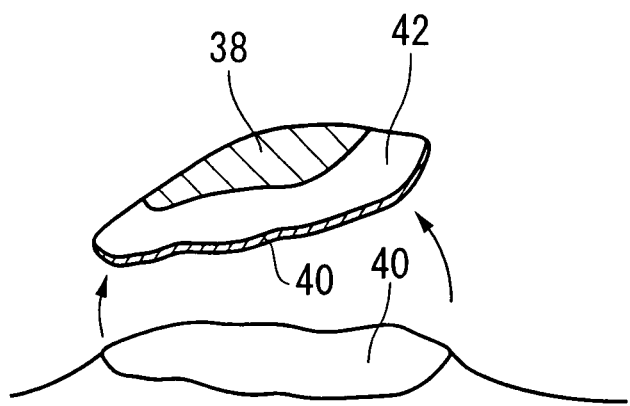
FIG. 12 is a perspective view showing a method for dissecting a submucosal layer using the same submucosal layer dissection system.

In this manner, by repeating the procedure from the hole opening step (S02) to the incision step (S06), submucosal layer 40 including affected area 38 is dissected as shown in FIGS. 11B and 11C and affected area 38 is separated as shown in FIG. 12.

Furthermore, there are cases in which the protuberance of affected area 38 contracts during the course of performing the aforementioned steps in the case of performing the dissection procedure over a wide range.

In this case, the procedure proceeds to the liquid injection step (S07).

Figure 13:
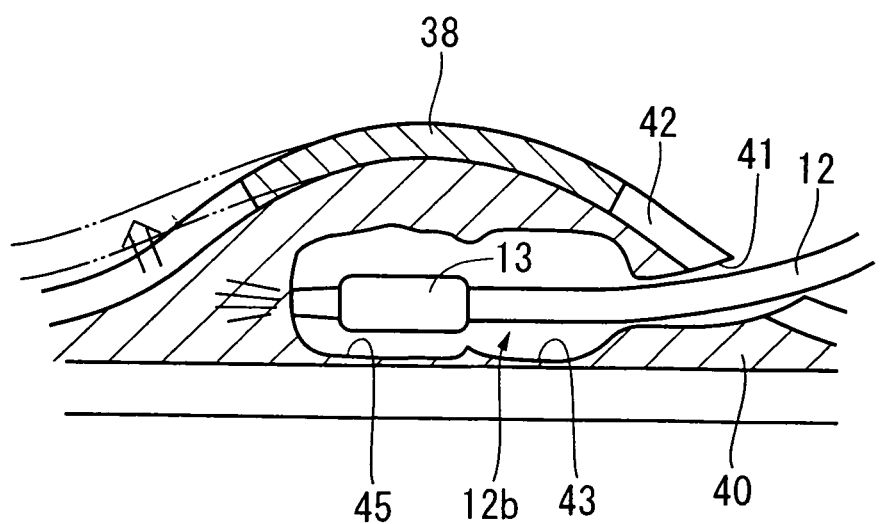
FIG. 13 is a cross-sectional view showing a method for dissecting a submucosal layer using the same submucosal layer dissection system.

First, as shown in FIG. 13, distal end 12b of instrument body 12 is arranged on the back side of second cavity 45, for example. A syringe 20 filled with a local injection liquid such as physiological saline is attached to liquid injection port 21 and the local injection liquid is injected into insertion path 18 from liquid injection port 21. As a result, similar to the elevation step (S01), the local injection liquid is injected into submucosal layer 40 causing affected area 38 to again become elevated.

Subsequently, the procedure returns to the step prior to proceeding to the liquid injection step (S07) and the procedure is resumed.

In addition, there are cases in which bleeding occurs accompanying dissection of submucosal layer 40 or incision with high-frequency scalpel 17. In such cases, the procedure proceeds to the hemostasis step (S08) and the irrigation step (S09).

Namely, in the case bleeding has been confirmed, distal end 12b of instrument body 12 is moved close to the area of bleeding in the hemostasis step (S08) to apply pressure to the area of bleeding by expanding balloon 13. Once hemostasis has been confirmed, the procedure proceeds to the irrigation step (S09) where distal end 12b of instrument body 12 is made to face in the direction of the area of bleeding. Local injection liquid is then released from distal end 12b of instrument body 12 by injecting a local injection liquid such as physiological saline into insertion path 18 from liquid injection port 21. Due to this, the area of bleeding is irrigated, and thereby a clear view of affected area 38 can be secured. In addition, an area of bleeding during submucosal layer dissection can be promptly stopped from bleeding, thereby making it possible to prevent complications incidental to the submucosal layer at the affected area in advance.

According to the submucosal layer dissection system 1 of the present embodiment as explained above, submucosal layer 40 can be dissected over a wide range by inserting balloon 13 into different sites of submucosal layer 40 and successively dissecting submucosal layer 40.

In addition, by inserting high-frequency scalpel 17 into insertion path 18 in advance, the periphery of affected area 38 can be incised by inserting high-frequency scalpel 17 into the dissected portion of submucosal layer 40 without having to interchange the instrument after having dissected submucosal layer 40 with balloon 13.

Moreover, since local injection liquid is made to pass through insertion path 18 in which high-frequency scalpel 17 is inserted from syringe 20 connected to liquid injection port 21, it is not necessary to provide a separate flow path for local injection liquid. Thus, the outer diameter of instrument body 12 can be made smaller thereby facilitating insertion into the body.

In addition, as a result of allowing local injection liquid to flow through insertion path 18, affected area 38 can be re-elevated by injecting local injection liquid into affected area 38 from insertion path 18 even if affected area 38 has returned to its original state after having been elevated during the dissection procedure of submucosal layer 40. In addition, since bleeding accompanying dissection of submucosal layer 40 or bleeding accompanying incision with high-frequency scalpel 17 can be promptly irrigated, a clear view of affected area 38 can be secured.

In addition, since distal end 12b of instrument body 12 employs a shape in which the outer diameter gradually becomes smaller moving towards distal end 12b, it can be easily inserted into submucosal layer 40. In addition, since the location of the distal end of balloon 13 is located at roughly the same location as distal end 12b of instrument body 12 during expansion of balloon 13, when dissecting submucosal layer 40 by inserting distal end 12b of instrument body 12 into submucosal layer 40, instrument body 12 can be prevented from being inserted into submucosal layer 40 farther to the back than the inserted location of distal end 12b.

In addition, the location of balloon 13 that has been inserted into submucosal layer 40 can be confirmed by observing indicator 22 with endoscope 6. Thus, only a desired section of submucosal layer 40 can be accurately dissected.

Figure 14:
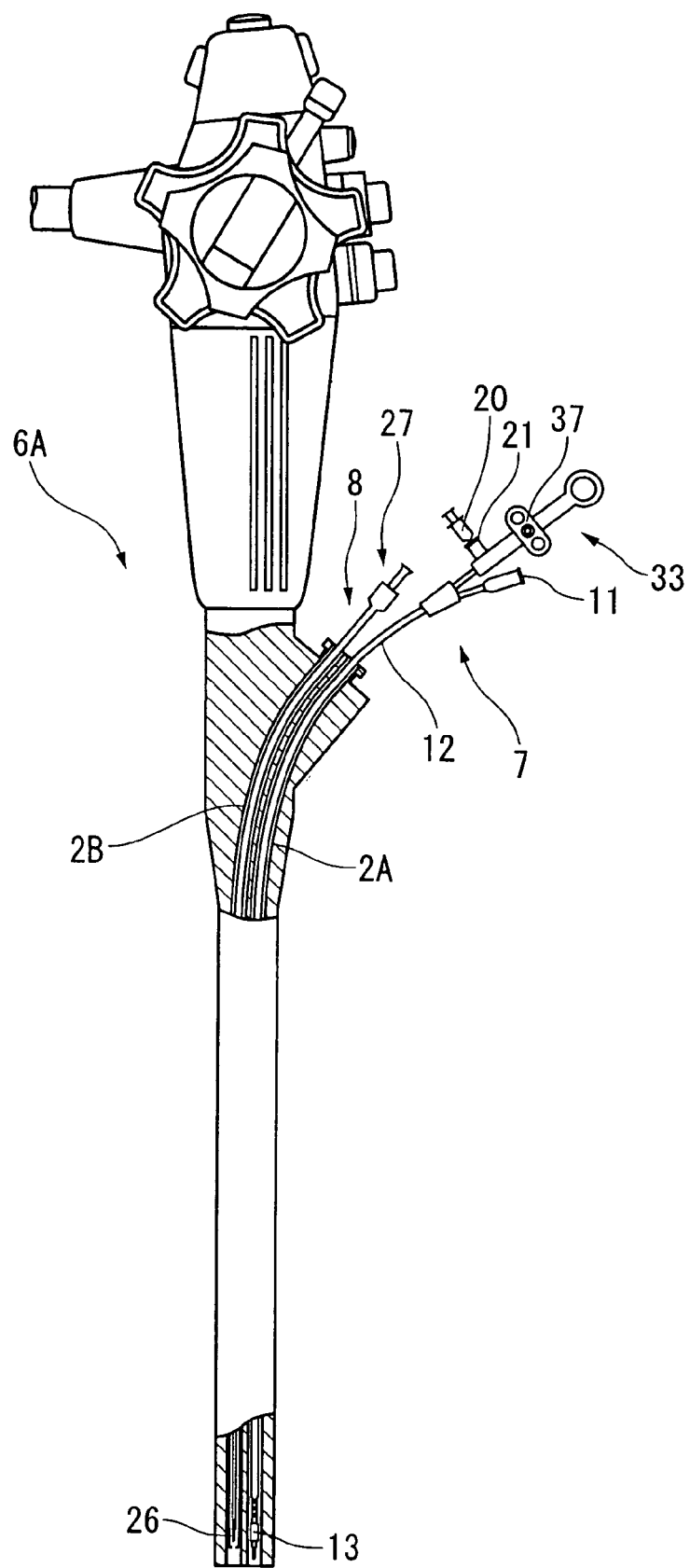
FIG. 14 is a side view including a partial cross-sectional view showing a variation of the same submucosal layer dissection system.

In addition, as shown in FIG. 14, an endoscope 6A in which two channels of a first channel 2A and a second channel 2B are arranged can be used by inserting dissection balloon 7 into first channel 2A and inserting submucosal injection needle 8 into second channel 2B. In this case, since both dissection balloon 7 and submucosal injection needle 8 can be inserted into the digestive tract together, the dissection procedure can proceed directly without having to interchange instruments after having elevated affected area 38 in the elevation step (S01). Thus, since the interchanging of instruments is reduced, the submucosal layer can be dissected easily and in a short period of time.

Figure 15:
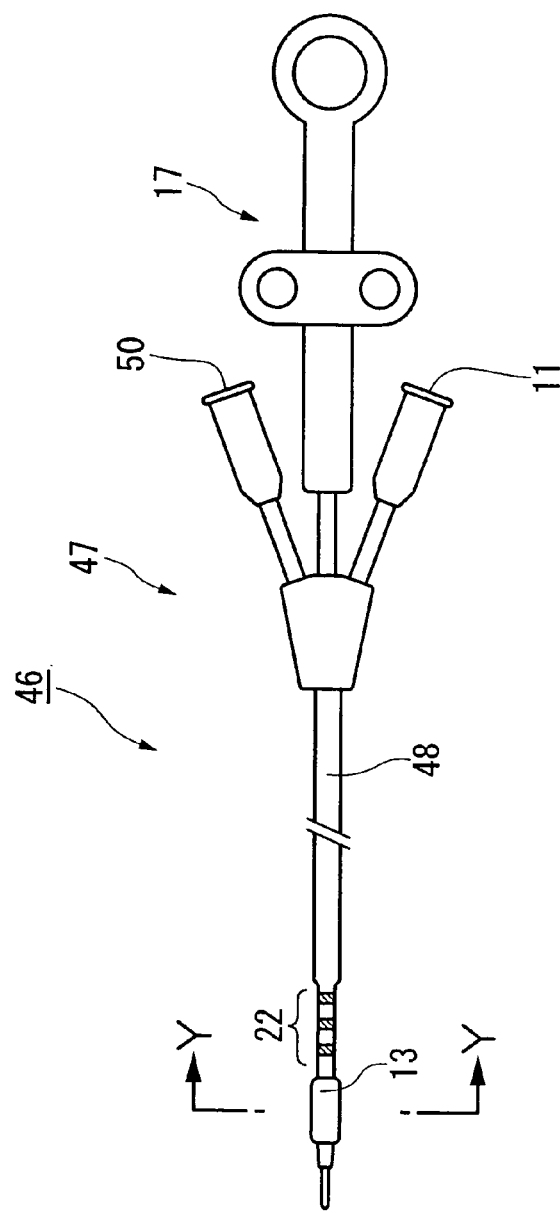
FIG. 15 is a side view showing a dissection balloon of a submucosal layer dissection system according to a second embodiment of the present invention.
Figure 16:
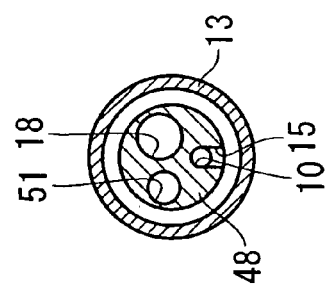
FIG. 16 is a cross-sectional view taken along Y-Y of FIG. 15.

Next, an explanation is provided of a second embodiment of the present invention with reference to FIGS. 15 and 16. Furthermore, the same reference symbols are used to the constituents of the second embodiment that are the same as the constituents of the first embodiment, and explanations thereof are omitted.

The difference between the present embodiment and the aforementioned first embodiment is that, an instrument body 48 of a dissection balloon 47 provided in a submucosal layer dissection system according to the present embodiment has a flow path 51 having a liquid injection port 50 provided in parallel with line 10 and insertion path 18 separate from insertion path 18 into which high-frequency scalpel 17 is inserted.

According to the submucosal layer dissection system 46, the procedure can be carried out with the same steps as in the aforementioned first embodiment, and the same action and effects can be obtained. Moreover, since insertion path 18 and flow path 51 are provided separately, in the case in which the local injection liquid injected into submucosal layer 40 has a high viscosity, the increase in fluid resistance can be prevented due to narrowing of the flow path of the local injection liquid caused by high-frequency scalpel 17. Thus, a flow path diameter that allows flow of the local injection liquid can be secured, and local injection liquid can be fed into the submucosal layer.

Figure 17:
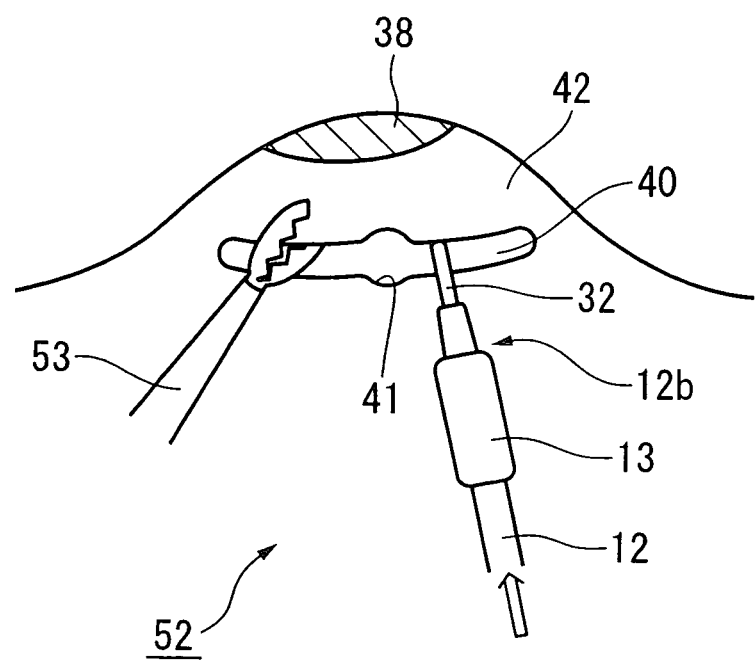
FIG. 17 is a perspective view showing a method for dissecting a submucosal layer using a submucosal layer dissection system according to a third embodiment of the present invention.

Next, an explanation of a third embodiment of the present invention is provided with reference to FIG. 17.

Furthermore, the same reference symbols are used to the same constituents as of the first embodiment, and explanations thereof are omitted.

The differences between the present embodiment and the aforementioned first embodiment are that, the submucosal layer dissection system 52 according to the present embodiment uses the endoscope 6A shown in FIG. 14, and a grasping forceps 53 is provided that is inserted into second channel 2B of endoscope 6A and able to support affected area 38 or submucosal layer 40.

In addition, in the method of dissecting a submucosal layer by using this submucosal layer dissection system 52, the present embodiment differs from the aforementioned first embodiment in that: submucosal injection needle 8 is firstly used by inserting it into first channel 2A, and thereafter submucosal injection needle 8 is interchanged with dissection balloon 7 for using it; and this method has a support step (S13) in which affected area 38 is supported using grasping forceps 53 during the insertion step and the incision step.

Namely, when the procedure proceeds to the insertion step (S03) and distal end 12b of instrument body 12 is inserted into hole 41, mucosa 42 and submucosal layer 40 are grasped and supported with grasping forceps 53 so as to facilitate insertion of instrument body 12 into submucosal layer 40.

As a result, since dissection balloon 7 can be easily inserted into submucosal layer 40, the procedure can be performed reliably in a short period of time.

In addition, when the procedure proceeds to the incision step (S06) and an incision is made by high-frequency knife 32, the target mucosa 42 and submucosal layer 40 are grasped and supported with grasping forceps 53 so that they can be fixed. As a result, the accuracy during incision increases and the procedure can be performed reliably.

Furthermore, after having inserted submucosal injection needle 8 into second channel 2B, submucosal injection needle 8 may be interchanged with grasping forceps 53, while dissection balloon 7 is kept inserted in first channel 2A.

While preferred embodiments of the present invention have been described and illustrated above, it should be understood that these are exemplary of the invention and are not to be considered as limiting. Additions, omissions, substitutions and other modifications can be made without departing from the spirit or scope of the present invention. Accordingly, the invention is not to be considered as being limited by the foregoing description, and is only limited by the scope of the appended claims.

Figure 18:
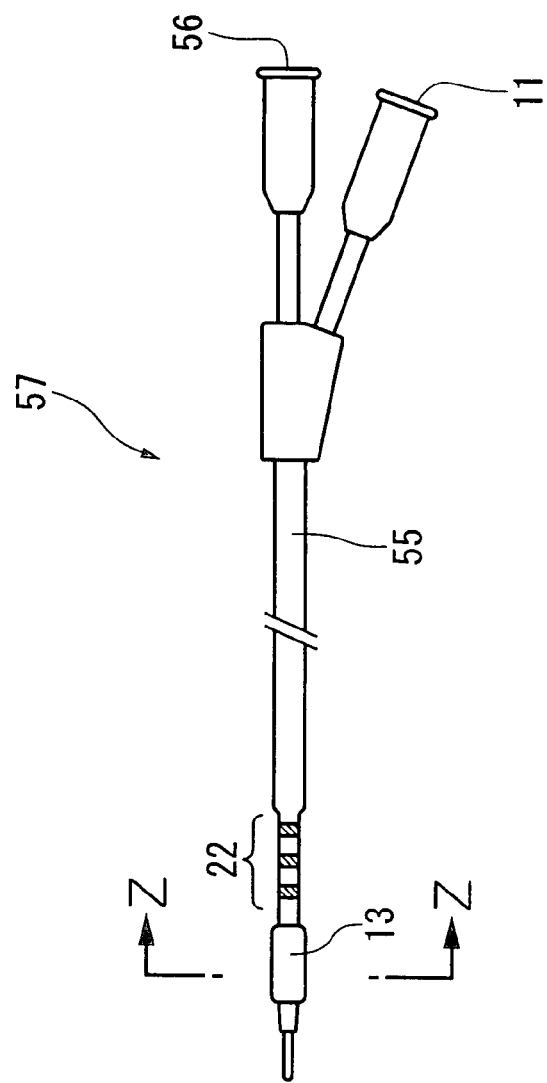
FIG. 18 is a side view of a dissection balloon that is a variation of the same submucosal layer dissection system.
Figure 19:
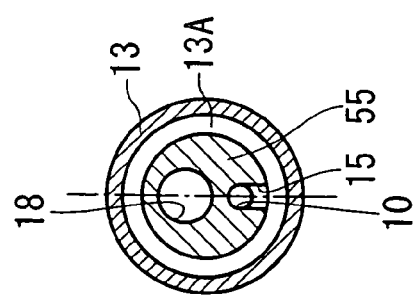
FIG. 19 is a cross-sectional view taken along Z-Z of FIG. 18.

For example, although dissection balloons 7 and 47 are both provided with a high-frequency scalpel 17 in each of the aforementioned embodiments, as shown in FIGS. 18 and 19, a dissection balloon 57 may be employed having a liquid injection port 56 directly on the proximal end of insertion path 18 of an instrument body 55 without containing a high-frequency incision instrument.

In addition, instead of the aforementioned second channel 2B, an externally connected channel along the lateral surface of insertion section 5 may be employed.

Moreover, the procedure using submucosal layer dissection system 1 is not limited to that described above, but rather only a portion of the abovementioned procedure may be performed.

As explained above, a submucosal layer dissection instrument of the present invention includes an instrument body that is inserted into a submucosal layer, a line formed between the proximal end side and the distal end side of the instrument body, and an expanding section provided on the distal end side of the instrument body that expands in the case of having received a supply of a fluid through the line.

According to the submucosal layer dissection instrument, the expanding section can be expanded within the submucosal layer to ablate the submucosal layer by inserting the distal end of the instrument body into the submucosal layer and supplying a fluid into the expanding section by making the fluid to flow into the line. Thus, a wide range of the submucosal layer can be dissected by inserting the expanding section into mutually different sites within the submucosal layer and successively dissecting the submucosal layer.

At that time, even if there is bleeding at an affected area within the submucosal layer, bleeding at that area can be stopped quickly by applying pressure to the area of bleeding by expanding the expanding section. Thus, complications incidental to the submucosal layer at the affected area can be prevented in advance.

Thus, according to the submucosal layer dissection instrument of the present invention, since the submucosal layer can be dissected without using a high-frequency scalpel many times as in the prior art, the procedure can be performed easily and the duration of the procedure can be shortened.

An insertion path into which a high-frequency scalpel is inserted may be provided along the line.

In this case, by inserting a high-frequency incision instrument into the insertion path in advance, the area around the affected area can be incised by inserting the high-frequency incision instrument into the dissected portion of the submucosal layer without having to interchange the instrument after having dissected the submucosal layer with the expanding section.

The instrument body may include a supply flow path for liquid to be injected into the submucosal layer.

In this case, even if an affected area that has been elevated ends up returning to its original state during the course of the dissection procedure of the submucosal layer, by supplying a liquid into the supply flow path, the liquid is injected from the supply flow path into the affected area, thereby making it possible to re-elevate the affected area. In addition, bleeding accompanying dissection of the submucosal layer or bleeding accompanying incision with the high-frequency incision instrument and so forth can be promptly irrigated, thereby making it possible to secure a clear view of the affected area.

The insertion path may also serves as a supply flow path for liquid injected into the submucosal layer.

In this case, since the insertion path through which a high-frequency incision instrument is inserted and the supply flow path through which a liquid is passed through are one in the same, the outer diameter of the instrument body can be made smaller, thereby making it easier to insert into the body.

The distal end of the instrument body may have a shape such that it tapers towards the distal end, and the location of the distal end of the expanding section during expansion may be made to coincide with the location of the distal end of the instrument body.

In this case, since the distal end of the instrument body is tapered, the instrument body can be easily inserted into the submucosal layer. In addition, since the location of the distal end of the expanding section during expansion coincides with the location of the distal end of the instrument body, when dissecting the submucosal layer by inserting the distal end of the instrument body into the submucosal layer, the instrument body can be prevented from being inserted to the back side of the submucosal layer beyond the location where the distal end of the expanding section is inserted.

An indicator that indicates the amount of insertion of the distal end of the insertion body may be provided on the instrument body on the proximal end side than the expanding section.

In this case, the insertion depth of the expanding section that has been inserted into the submucosal layer can be confirmed by observing this indicator, thereby making it possible to accurately ablate a desired portion of the submucosal layer.

A submucosal layer dissection system of the present invention includes an endoscope in which a first channel and a second channel are provided, the abovementioned submucosal layer dissection instrument that is inserted into the first channel, and a submucosal injection needle inserted into the second channel, which injects a liquid into the submucosal layer.

According to the submucosal layer dissection system, since the aforementioned submucosal layer dissection instrument is provided, interchanging of instruments can be reduced when dissecting the submucosal layer by inserting the distal end into the submucosal layer in order to resect an affected area of the digestive tract. Thus, the submucosal layer can be dissected easily and in a short period of time. In addition, by using an endoscope having two channels, the submucosal layer dissection instrument and submucosal injection needle can be inserted into the digestive tract together. Thus, the procedure can be proceed directly to the dissection procedure without having to interchange the instrument after having elevated the affected area.

Another submucosal layer dissection system of the present invention includes an endoscope in which a first channel and a second channel are provided, the abovementioned submucosal layer dissection instrument that is inserted into the first channel, and a grasping forceps inserted into the second channel, which supports the submucosal layer.

According to the submucosal layer dissection system, since the aforementioned submucosal layer dissection instrument is provided, interchanging of instruments can be reduced when dissecting the submucosal layer by inserting the distal end into the submucosal layer in order to resect an affected area of the digestive tract. Thus, the submucosal layer can be dissected easily and in a short period of time. In addition, by using an endoscope having two channels, the submucosal layer dissection instrument and grasping forceps can be inserted into the digestive tract together. Thus, when dissecting the submucosal layer, the submucosal layer dissection instrument can be easily inserted into the submucosal layer while supporting the affected area.

A first submucosal layer dissection method of the present invention includes an insertion step in which the abovementioned submucosal layer dissection instrument is inserted into elevated submucosal layer, and a dissection step in which the expanding section of the submucosal layer dissection instrument is expanded by supplying a fluid thereto followed by dissection of the submucosal layer.

According to the first submucosal layer dissection method, the submucosal layer near an affected area can be easily dissected in a short period of time.

The first submucosal layer dissection method may further include a hemostasis step in which an area of bleeding of the submucosal layer is stopped from bleeding by applying pressure with the expanding section.

In this case, since bleeding during dissection of the submucosal layer can be stopped promptly, complications incidental to the submucosal layer at the affected area can be prevented in advance.

A second submucosal layer dissection method of the present invention includes a hole opening step in which a hole is opened in mucosa that covers a submucosal layer with a high-frequency incision instrument, an insertion step in which the distal end of the instrument body of the abovementioned submucosal layer dissection instrument is inserted into the hole, a dissection step in which the submucosal layer is dissected by supplying a fluid into the expanding section to expand it, and an incision step in which at least one of the mucosa around the hole and the submucosal layer is incised using the high-frequency incision instrument.

According the second submucosal layer dissection method, since the submucosal layer can be incised by a high-frequency incision instrument in addition to dissecting the submucosal layer, the submucosal layer can be dissected over a desired wide range easily and in a short period of time.

A third submucosal layer dissection method of the present invention includes a hole opening step in which a hole is opened in mucosa that covers a submucosal layer with a high-frequency incision instrument, an insertion step in which the distal end of the instrument body of the abovementioned submucosal layer dissection instrument which includes the supply flow path for liquid to be injected into the submucosal layer, is inserted into the hole, a dissection step in which the submucosal layer is dissected by supplying a fluid into the expanding section to expand it, an incision step in which at least one of the mucosa around the hole and the submucosal layer is incised using the high-frequency incision instrument, and a liquid injection step in which the liquid is injected into the supply flow path to elevate the submucosal layer.

According to the third submucosal layer dissection method, an affected area can be re-elevated without having to interchange instruments by injecting a liquid even if the protuberance of the affected area has returned to its original state during the dissection procedure of the submucosal layer.

The third submucosal layer dissection method may further include an irrigation step in which bleeding within the submucosal layer is irrigated by injecting the liquid into the supply flow path.

In this case, bleeding accompanying dissection of the submucosal layer or bleeding and so forth accompanying incision with the high-frequency incision instrument can be promptly irrigated, thereby ensuring a clear view of the affected area.

A fourth submucosal layer dissection method of the present invention includes: a hole opening step in which a hole is opened in mucosa that covers a submucosal layer with a high-frequency incision instrument; an insertion step in which the distal end of the instrument body of the abovementioned submucosal layer dissection instrument which has a shape such that it tapers towards the distal end, and in which the location of the distal end of the expanding section during expansion be made to coincide with the location of the distal end of the instrument body, is inserted into the hole; a positioning step in which the location of the distal end of the instrument body is aligned with the dissected location of the submucosal layer; a dissection step in which the submucosal layer is dissected by supplying a fluid into the expanding section to expand it; and an incision step in which at least one of the mucosa around the hole and the submucosal layer is incised using the high-frequency incision instrument.

According to the fourth submucosal layer dissection method, the submucosal layer can be dissected safely at a desired depth during dissection of the submucosal layer.

A fifth submucosal layer dissection method of the present invention includes: a hole opening step in which a hole is opened in mucosa that covers a submucosal layer with a high-frequency incision instrument; an insertion step in which the distal end of the instrument body of the abovementioned submucosal layer dissection instrument in which the indicator that indicates the amount of insertion of the distal end of the insertion body be provided on the instrument body on the proximal end side than the expanding section, is inserted into the hole; a positioning step in which the location of the distal end of the instrument body is aligned with the dissected location of the submucosal layer based on the indicator; a dissection step in which the submucosal layer is dissected by supplying a fluid into the expanding section to expand it; and an incision step in which at least one of the mucosa around the hole and the submucosal layer is incised using the high-frequency incision instrument.

According to the fifth submucosal layer dissection method, the insertion depth of the expanding section into the submucosal layer can be accurately determined by an indicator. Thus, the submucosal layer can be dissected safely since the dissection depth can be accurately determined.

A sixth submucosal layer dissection method of the present invention includes an elevation step in which the submucosal layer is elevated by injecting a liquid into the submucosal layer using the submucosal injection needle of the abovementioned submucosal layer dissection system, an insertion step in which the submucosal layer dissection instrument is inserted into the elevated submucosal layer, and a dissection step in which the submucosal layer is dissected by supplying a fluid into the expanding section of the submucosal layer dissection instrument to expand it.

According to the sixth submucosal layer dissection method, after having elevated the affected area, the procedure can proceed immediately to the insertion step without having to newly insert the submucosal layer dissection instrument after retracting the submucosal layer dissection instrument from the endoscope. Thus, the procedure can be performed in a short period of time.

A seventh submucosal layer dissection method of the present invention includes a support step in which the submucosal layer is supported using the grasping forceps of the abovementioned another submucosal layer dissection system, an insertion step in which the submucosal layer dissection instrument is inserted into the elevated submucosal layer, and a dissection step in which the submucosal layer is dissected by supplying a fluid into the expanding section of the submucosal layer dissection instrument to expand it.

According to the seventh submucosal layer dissection method, the submucosal layer dissection instrument can be easily inserted into the submucosal layer as a result of supporting with the grasping forceps. In addition, since the incision procedure can be performed accurately by a high-frequency incision instrument, the procedure can be performed reliably in a short period of time.

What is claimed is:

1. A submucosal layer dissection method using a submucosal layer dissection instrument comprising:
    an instrument body having an insertion path which is provided along an axial direction of the instrument body and which has a distal end opening positioned at a distal end portion of the instrument body;
    an incision instrument disposed inside the insertion path so as to be capable of protruding from and retracting from the distal end opening of the instrument body; and
    an expanding section which is provided on an outer surface of the distal end portion of the instrument body that is capable of expanding in a case of having received a supply of a fluid, a distal end part of the expanding section being positioned at the distal end portion of the instrument body when the expanding section is expanded; the method comprising:
    elevating an affected area of the digestive tract by supplying liquid into the submucosal layer;
    subsequent to the elevating, inserting the distal end portion of the instrument body which includes the expanding section into the submucosal layer; and
    subsequent to the inserting, expanding the expanding section until the distal end part of the expanding section is positioned at a same position of the distal end portion of the instrument body in the axial direction by supplying the fluid thereto until the submucosal layer is dissected by an expansion force of the expanding section while the incision instrument is inserted into the insertion path.

2. The submucosal layer dissection method according to claim 1, further comprising a hemostasis step in which an area of bleeding of the submucosal layer is stopped from bleeding by applying pressure with the expanding section.

3. The submucosal layer dissection method using the submucosal layer dissection instrument according to claim 1, comprising:
wherein the incision instrument is a high-frequency incision instrument, the method comprising:
opening a hole in a mucosa which covers the submucosal layer using the high-frequency incision instrument;
inserting the distal end portion of the instrument body of the submucosal layer dissection instrument into the hole; and
incising at least one of the mucosa around the hole and the submucosal layer by using the high-frequency incision instrument.

4. The submucosal layer dissection method using the submucosal layer dissection instrument according to claim 3,
wherein the liquid is supplied through the insertion path to the submucosal layer while the affected area of the digestive tract is elevated.

5. The submucosal layer dissection method using the submucosal layer dissection instrument according to claim 4, further comprising:
positioning the location of the distal end portion of the instrument body to be aligned with the dissected location of the submucosal layer wherein
the distal end portion of the instrument body includes a tapered portion which is tapered towards a distal end of the instrument body.

6. The submucosal layer dissection method using the submucosal layer dissection instrument according to claim 3, the submucosal layer dissection instrument further comprising an indicator that indicates the amount of insertion of the distal end portion of the insertion body provided at a location of the instrument body that is more proximal than that of the expanding section,
the method further comprising:
positioning the location of the distal end portion of the instrument body to be aligned with the dissected location of the submucosal layer based on the indicator.

7. The submucosal layer dissection method using the submucosal layer dissection instrument according to claim 6, further comprising endoscopically separating the affected area of the digestive tract by repeating the method.

8. The submucosal layer dissection method using the submucosal layer dissection instrument according to claim 3, further comprising:
incising at least one of the mucosa around the hole and the submucosal layer.

9. The submucosal layer dissection method according to claim 1, further comprising an irrigation step in which bleeding within the submucosal layer is irrigated by injecting the liquid into the insertion path.

10. The submucosal layer dissection method using the submucosal layer dissection instrument according to claim 1, the submucosal layer dissection instrument further comprising a fluid passage arranged in parallel with the insertion path; and
wherein the expanding section is expanded by supplying the fluid through the fluid passage.

11. The submucosal layer dissection method according to claim 1, further comprising an incision step subsequent to the expanding step, the incision step comprising incising at least the dissected submucosal layer.

12. A submucosal layer dissection method using a submucosal layer dissection system comprising:
an endoscope in which a first channel and a second channel are provided;
a submucosal dissection instrument inserted into the first channel comprising:
an instrument body having an insertion path and a fluid passage extending in an axial direction thereof, the insertion path having a distal end opening positioned at a distal end portion of the instrument body, an injection port provided at a proximal end side of the insertion body, the injection port being connected to the fluid passage;
an incision instrument disposed inside the insertion path so as to be capable of protruding from and retracting from the distal end opening of the instrument body; and
an expanding section provided on the distal end portion of the instrument body that is capable of expanding when receiving a supply of a fluid from the injection port; wherein
a distal end part of the expanding section is at a distal end portion of the instrument body when the expanding section is expanded; and
a submucosal injection needle inserted into the second channel, which injects a liquid into the submucosal layer, the method comprising:
elevating the submucosal layer by injecting a liquid into the submucosal layer using the submucosal injection needle of the submucosal layer dissection system;
inserting the submucosal layer dissection instrument into the elevated submucosal layer; and
dissecting the submucosal layer by supplying a fluid into the expanding section of the submucosal layer dissection instrument to expand the expanding section while the incision instrument is inserted into the insertion path.

13. The submucosal layer dissection method using the submucosal layer dissection system according to claim 12,
the submucosal layer dissection instrument further comprising:
a grasping forceps inserted into the second channel, which supports the submucosal layer, and the method further comprising:
supporting the submucosal layer using the grasping forceps.

* * * * *